(12) United States Patent
Govari et al.

(10) Patent No.: US 9,986,949 B2
(45) Date of Patent: Jun. 5, 2018

(54) MULTI-ARM CATHETER WITH SIGNAL TRANSMISSION OVER BRAID WIRES

(71) Applicant: BIOSENSE WEBSTER (ISRAEL) LTD., Yokneam (IL)

(72) Inventors: Assaf Govari, Haifa (IL); Christopher Thomas Beeckler, Brea, CA (US)

(73) Assignee: BIOSENSE WEBSTER (ISRAEL) LTD., Yokneam (IL)

(*) Notice: Subject to any disclaimer, the term of this patent is extended or adjusted under 35 U.S.C. 154(b) by 79 days.

(21) Appl. No.: 14/197,775

(22) Filed: Mar. 5, 2014

(65) Prior Publication Data

US 2015/0250424 A1    Sep. 10, 2015

(51) Int. Cl.

| | | |
|---|---|---|
| *A61B 18/18* | (2006.01) | |
| *A61B 5/04* | (2006.01) | |
| *A61B 5/00* | (2006.01) | |
| *A61B 18/08* | (2006.01) | |
| *A61B 18/14* | (2006.01) | |
| *A61B 5/042* | (2006.01) | |
| *A61B 5/06* | (2006.01) | |

(Continued)

(52) U.S. Cl.
CPC .......... *A61B 5/6858* (2013.01); *A61B 5/0422* (2013.01); *A61B 5/062* (2013.01); *A61B 5/6859* (2013.01); *A61B 5/6886* (2013.01); *A61B 18/082* (2013.01); *A61B 18/1492* (2013.01); *A61B 2018/00267* (2013.01); *A61B 2018/00351* (2013.01); *A61B 2018/00577* (2013.01); *A61B 2018/00839* (2013.01); *A61B 2034/2053* (2016.02)

(58) Field of Classification Search
CPC ...... A61B 18/1492; A61B 2018/00214; A61B 2018/00267; A61B 2018/00577; A61B 2018/0022; A61B 2018/00839; A61B 2019/5466; A61B 5/6858; A61B 2017/22038; A61B 2018/00178; A61B 2018/00351; A61M 25/0108; A61M 25/10; A61M 25/1011

USPC ........ 600/372–374, 377, 380–381, 393, 435, 600/481, 508–509; 607/115, 122–124

See application file for complete search history.

(56) References Cited

U.S. PATENT DOCUMENTS

| | | | |
|---|---|---|---|
| 5,391,199 A | | 2/1995 | Ben-Haim |
| 5,558,073 A | * | 9/1996 | Pomeranz ............ A61B 5/0422 600/374 |

(Continued)

FOREIGN PATENT DOCUMENTS

| | | |
|---|---|---|
| EP | 1393674 A1 | 3/2004 |
| WO | WO 96/05768 A1 | 2/1996 |

OTHER PUBLICATIONS

European Search Report dated Jul. 10, 2015 for corresponding Application No. EP15157596.6.

*Primary Examiner* — Joseph Stoklosa
*Assistant Examiner* — Brian M Antiskay
(74) *Attorney, Agent, or Firm* — Notaro, Michalos & Zaccaria P.C.

(57) ABSTRACT

A medical probe includes an insertion tube for insertion into a patient's body, and multiple arms that are attached to a distal end of the insertion tube. Each arm includes a braid of wires that traverse the arm. Multiple electrodes are coupled to the arms and electrically connected to respective selected wires of the braid. The electrodes are configured to exchange signals over the wires with a system external to the patient body.

5 Claims, 4 Drawing Sheets

(51) Int. Cl.
  *A61B 18/00* (2006.01)
  *A61B 34/20* (2016.01)

(56) References Cited

U.S. PATENT DOCUMENTS

| | | | |
|---|---|---|---|
| 5,598,848 A * | 2/1997 | Swanson et al. | 600/508 |
| 5,722,402 A | 3/1998 | Swanson et al. | |
| 6,009,877 A * | 1/2000 | Edwards | A61B 5/04884 |
| | | | 128/898 |
| 6,088,610 A | 6/2000 | Littmann et al. | |
| 6,239,724 B1 | 5/2001 | Doron et al. | |
| 6,292,703 B1 | 9/2001 | Meier et al. | |
| 6,332,089 B1 | 12/2001 | Acker et al. | |
| 6,484,118 B1 | 11/2002 | Govari | |
| 6,574,492 B1 | 6/2003 | Ben-Haim et al. | |
| 6,618,612 B1 | 9/2003 | Acker et al. | |
| 6,690,963 B2 | 2/2004 | Ben-Haim et al. | |
| 7,089,045 B2 | 8/2006 | Fuimaono et al. | |
| 7,881,769 B2 | 2/2011 | Sobe | |
| 8,226,580 B2 | 7/2012 | Govari et al. | |
| 2002/0065455 A1 | 5/2002 | Ben-Haim et al. | |
| 2003/0088244 A1 | 5/2003 | Swanson et al. | |
| 2003/0120150 A1 | 6/2003 | Govari | |
| 2003/0191449 A1 * | 10/2003 | Nash | A61B 17/32037 |
| | | | 604/523 |
| 2004/0068178 A1 | 4/2004 | Govari | |
| 2004/0162600 A1 * | 8/2004 | Williams | 607/122 |
| 2006/0235286 A1 * | 10/2006 | Stone et al. | 600/381 |
| 2012/0116254 A1 * | 5/2012 | Morriss | A61B 5/411 |
| | | | 600/587 |
| 2012/0182014 A1 | 7/2012 | Rivera et al. | |
| 2014/0309512 A1 * | 10/2014 | Govari | A61N 1/05 |
| | | | 600/374 |

* cited by examiner

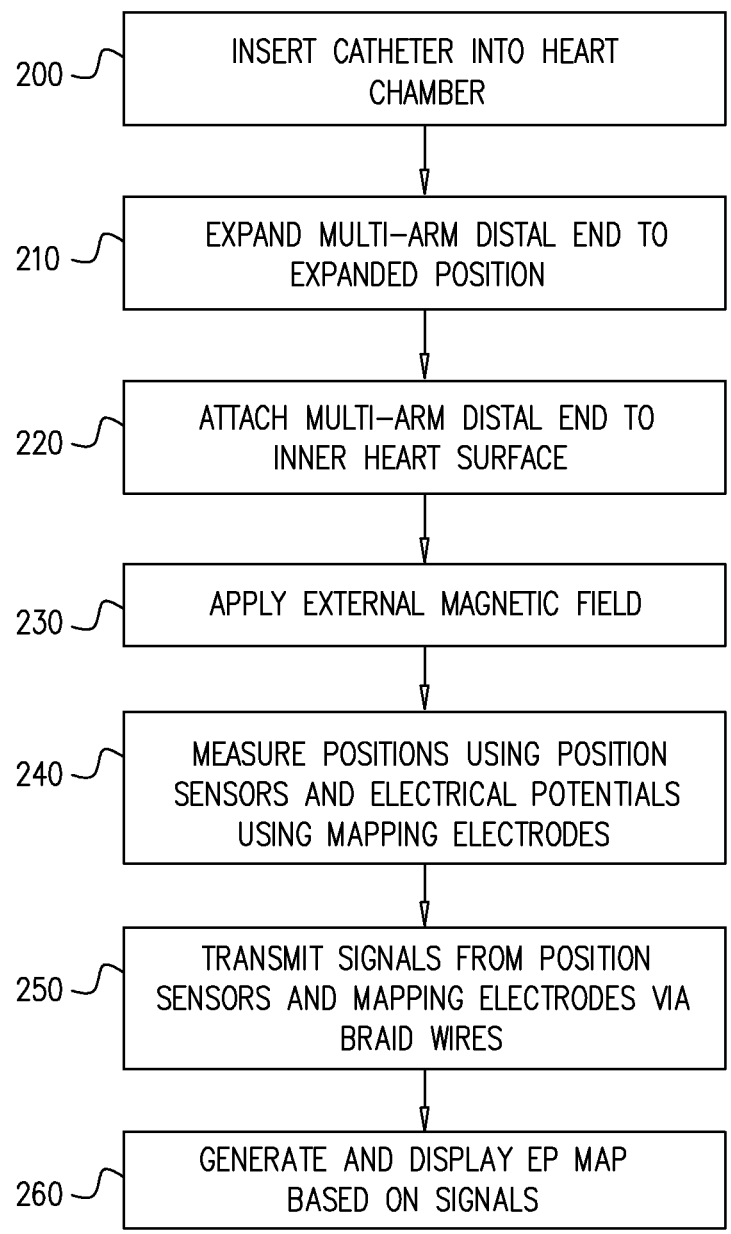

MULTI-ARM CATHETER WITH SIGNAL TRANSMISSION OVER BRAID WIRES

FIELD OF THE INVENTION

The present invention relates generally to invasive medical devices, and particularly to multi-arm medical probes.

BACKGROUND OF THE INVENTION

Various types of diagnostic and therapeutic sensors and electrodes may be located at the distal end of medical probes for positioning, mapping and/or treatment applications. The sensors or electrodes at the distal end of the probe are typically connected to an external system via wires traversing the probe.

For example, U.S. Pat. No. 7,881,769, whose disclosure is incorporated herein by reference, describes a catheter for performing a medical operation on an organic lumen, the catheter including an elongated member, a medical operational element located at a distal end of the elongated member, an electromagnetic field detector located at the distal end, and a wiring for coupling the electromagnetic field detector with a medical positioning system, wherein the medical positioning system determines the position and orientation of the distal end.

U.S. Patent Application Publication 2012/0182014, whose disclosure is incorporated herein by reference, describes a magnetic resonance imaging device, which includes an elongate flexible member having a proximal end, a distal end, and a lumen extending between the proximal end and the distal end and a solenoid coil affixed to the distal end of the elongate flexible member, the solenoid coil having a plurality of wire turns, the solenoid coil connected to a twisted-pair of leads extending proximally along the length of the flexible member. A connector is disposed at the proximal end of the elongate flexible member, the connector operatively coupled to the twisted-pair of leads. In an alternative embodiment, a coaxial cable substitutes for the lumen-containing elongate flexible member.

Some medical probes have distal ends that comprise multiple arms and/or multiple electrodes. For example, U.S. Pat. No. 5,722,402, whose disclosure is incorporated herein by reference, describes systems and related methods for guiding a movable electrode within an array of multiple electrodes located within the body. The systems and methods employ the movable electrode or at least one of the multiple electrodes on the array to generate and then sense electrical or sonic energy in a predetermined fashion to generate an output that locates the movable electrode within the array.

U.S. Pat. No. 6,574,492, whose disclosure is incorporated herein by reference, describes a catheter for measuring physiological signals in a heart. The catheter comprises a structure at a distal end of the catheter wherein the structure has a plurality of arms, an electrode fixed to each arm and a device for generating position information located on each arm. The arms are located near the long axis of the catheter during insertion of the catheter within a heart and the arms are spreadable apart and away from the long axis of the catheter when the structure is within the heart.

U.S. Pat. No. 8,226,580, whose disclosure is incorporated herein by reference, describes a method for operating a medical probe. The method includes pressing a distal end of the medical probe, which includes one or more arms that extend diagonally outward from a central shaft and have respective position transducers coupled thereto, against an intra-body surface, so as to cause the arms to exert pressure on the surface and bend with respect to the central shaft in response to the pressure. Positions of the respective position transducers coupled to the arms are measured, and the pressure exerted by the arms is estimated responsively to the measured positions.

U.S. Pat. No. 7,089,045, whose disclosure is incorporated herein by reference, describes a catheter for mapping the Purkinje fibers for potential diagnosis of ventricular fibrillation. The catheter comprises an elongated catheter body having proximal and distal ends and at least one lumen extending longitudinally there through. Mounted at the distal end of the catheter body is a mapping assembly having at least two spines, each having a proximal end attached at the distal end of the catheter body and a free distal end. Each spine comprises at least one electrode, preferably a tip electrode and at least one ring electrode. The spines may be arranged in an expanded arrangement wherein each spine extends radially outwardly from the catheter body or in a collapsed arrangement wherein each spine is disposed generally along the longitudinal axis of the catheter body.

SUMMARY OF THE INVENTION

An embodiment of the present invention that is described herein provides a medical probe including an insertion tube for insertion into a patient body, and multiple arms that are attached to a distal end of the insertion tube. Each arm includes a braid of wires that traverse the arm. Multiple electrodes are coupled to the arms and electrically connected to respective selected wires of the braid. The electrodes are configured to exchange signals over the wires with a system external to the patient body.

In some embodiments, one or more of the electrodes include electrophysiological (EP) mapping electrodes that are configured to produce the signals in response to measured EP potential. In an embodiment, one or more of the electrodes include ablation electrodes that are configured to perform ablation of tissue in response to an ablation signal. In another embodiment, the medical probe includes one or more position sensors, which are coupled to the arms and electrically connected to respective selected wires of the braid, and which are configured to produce position signals that are indicative of respective positions in the patient body, and to transfer the position signals over the wires.

In yet another embodiment, the multiple arms are expandable into a basket configuration. In still another embodiment, the braid of wires in each arm is coiled. In an example embodiment, the selected wires of the braid are electrically isolated.

There is additionally provided, in accordance with an embodiment of the present invention, a method including inserting into a patient body a medical probe, which includes an insertion tube and multiple arms attached to a distal end of the insertion tube. The arms include respective braids of wires that traverse the arms and multiple electrodes that are electrically connected to respective selected wires of the braids. Signals are exchanged over the wires between the electrodes and a system external to the patient body.

There is further provided, in accordance with an embodiment of the present invention, a method including providing an insertion tube for insertion into a patient body. Multiple arms are attached to a distal end of the insertion tube multiple arms, each arm including a braid of wires that traverse the arm. Multiple electrodes are coupled to the arms, and the electrodes are electrically connected to respective selected wires of the braid, so as to exchange signals over the wires with a system external to the patient body.

The present invention will be more fully understood from the following detailed description of the embodiments thereof, taken together with the drawings in which:

BRIEF DESCRIPTION OF THE DRAWINGS

FIG. 4 is a flow chart that schematically illustrates a method for electrical potential mapping using the catheter of FIG. 3, in accordance with an embodiment of the present invention.

DETAILED DESCRIPTION OF EMBODIMENTS

Overview

Medical probes such as catheters are used in a variety of therapeutic and diagnostic medical procedures. The distal end of a probe may comprise various kinds of electrodes and sensors, such as electrophysiological (EP) mapping electrodes and/or position sensors. The signals sensed by the sensors and electrodes are typically transmitted from the distal end using suitable wires. In some types of probes, e.g., multi-arm catheters, the number of sensors and electrodes (and therefore the number of wires) may be large.

Embodiments of the present invention that are described herein below provide improved techniques for transferring electrical signals from the distal end of a multi-arm probe. In some embodiments, the distal end comprises multiple arms, and each arm comprises one or more EP mapping electrodes and one or more position sensors.

Each arm further comprises a braid of wires that serves a dual purpose: Providing structural mechanical support for the arm, and conducting the signals sensed by the sensors and electrodes from the distal end to the system's control console. Typically, each sensor or electrode is connected to the control console via by a respective pair of wires selected from among the braid wires of the corresponding arm.

Since the disclosed techniques re-use the existing braid wires for signal transmission, they eliminate the need for additional cabling that traverse the catheter lumen, as well as for additional shielding. This saving in volume can be used for vacating the catheter lumen for other purposes, or for reducing the catheter diameter.

The disclosed techniques are particularly important in multi-arm catheters, which typically comprise a large number of electrodes and sensors. Since the probe diameter is constrained, having to route the signals over wires running through the central lumen of the probe would severely limit the possible number of electrodes and sensors. The disclosed techniques remove this limitation and enable the use of any desired number of electrodes and sensors, with little or no impact on the probe diameter.

The disclosed techniques can be used with various multi-arm structures, such as expandable basket catheters or any other suitable configuration. Moreover, the disclosed techniques are not limited to position sensors and mapping electrodes. For example, braid wires can be used for transferring ablation signals to ablation electrodes.

System Description

Figure 1:
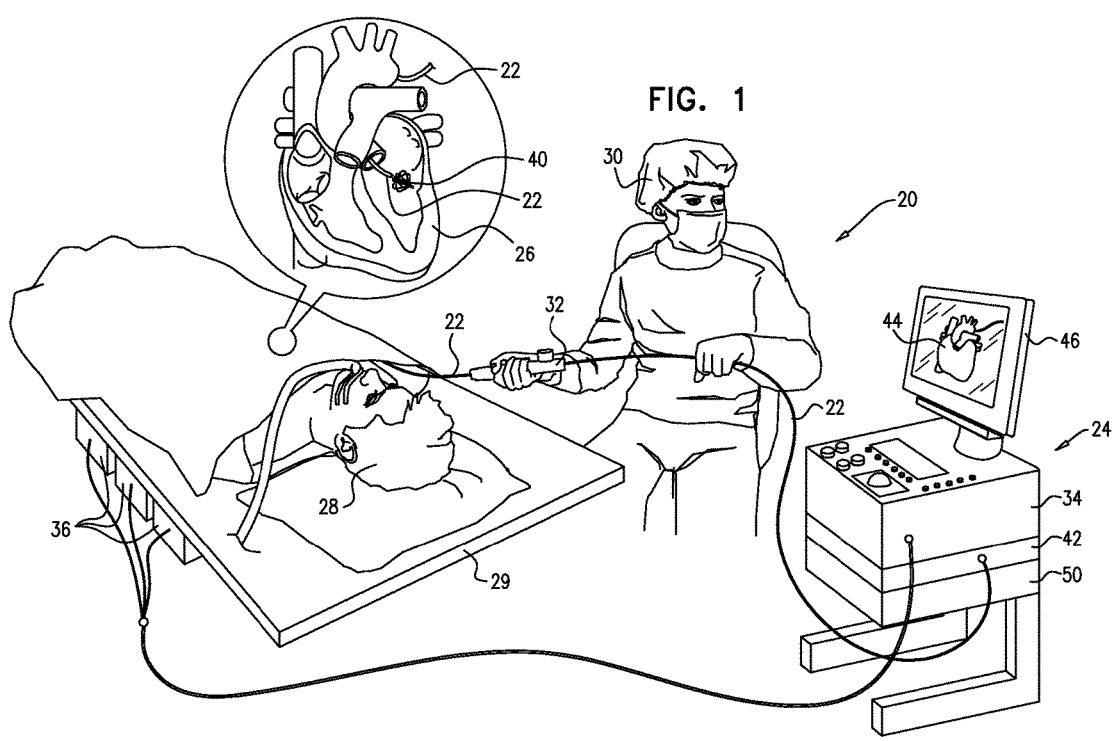
FIG. 1 is a schematic, pictorial illustration of a catheter tracking system, in accordance with an embodiment of the present invention.

FIG. 1 is a schematic, pictorial illustration of a catheter tracking system 20, in accordance with an embodiment of the present invention. System 20 comprises a probe 22, in the present example a cardiac catheter, and a control console 24. In the embodiment described herein, catheter 22 may be used for any suitable therapeutic and/or diagnostic purposes, such as ablation of tissue in a heart 26 and the mapping of electro-cardiac signals for the diagnosis of cardiac dysfunctions, such as cardiac arrhythmias, for example.

Console 24 comprises a processor 42, typically a general-purpose computer, with suitable front end and interface circuits for receiving signals from catheter 22 and for controlling the other components of system 20 described herein. Processor 42 may be programmed in software to carry out the functions that are used by the system, and the processor stores data for the software in a memory 50. The software may be downloaded to console 24 in electronic form, over a network, for example, or it may be provided on non-transitory tangible media, such as optical, magnetic or electronic memory media. Alternatively, some or all of the functions of processor may be carried out by dedicated or programmable digital hardware components.

An operator 30 (such as an interventional cardiologist) inserts catheter 22 through the vascular system of a patient 28 lying on a table 29. Catheter 22 comprises an insertion tube, and a multi-arm that is part of distal end 40. Operator 30 moves distal end 40 of catheter 22 in the vicinity of the target region in heart 26 by manipulating catheter 22 with a manipulator 32 near the proximal end of the catheter as shown in the inset of FIG. 1. The proximal end of catheter 22 is connected to interface circuitry in processor 42.

The position of the distal end of the probe in the heart cavity is typically measured by magnetic position sensing in catheter tracking system 20. In this case, console 24 comprises a driver circuit 34, which drives magnetic field generators 36 placed at known positions external to patient 28 lying on table 29, e.g., below the patient's torso.

Distal end 40 typically comprises multiple arms, each comprising one or more magnetic field sensors and one or more mapping electrodes (shown in FIGS. 2 and 3 below). When the distal end is brought into contact with the inner heart surface, the mapping electrodes generate potential gradient signals in response to the sensed electrical potentials and the position sensors generate position signals in response to the sensed external magnetic fields, thereby enabling processor 42 to map the electrical potentials as a function of position within the heart cavity.

The multiple magnetic position sensors and mapping electrodes in distal end 40 are connected to interface circuitry in processor 42 at the catheter proximal end. Operator 30 can view the position of catheter distal end 40 on an image 44 of heart 26 on a user display 46.

This method of position sensing is implemented, for example, in the CARTO™ system, produced by Biosense Webster Inc. (Diamond Bar, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

Use of Catheter Braid Wires for Signal Transmission

Figure 2:
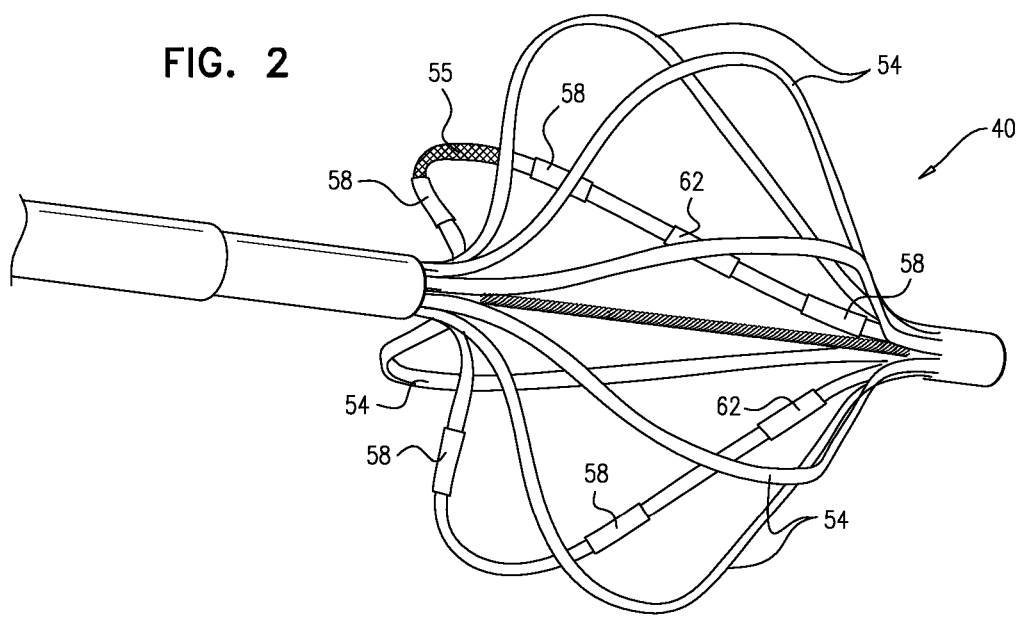
FIG. 2 is a schematic, pictorial illustration of a multi-arm catheter in expanded position, in accordance with an embodiment of the present invention.

FIG. 2 is a schematic, pictorial illustration of distal end 40 of catheter 22, in accordance with an embodiment of the present invention. In this embodiment, distal end 40 (which is connected to the insertion tube of the catheter) comprises multiple arms 54. During insertion of the catheter, the arms are grouped together in a collapsed position. After insertion into the heart cavity of interest, the arms are set to an expanded position as shown in FIG. 2.

Each arm 54 comprises embedded sensors or electrodes, such as one or more mapping electrodes 58, one or more position sensors 62, or any other type of sensors or electrodes. At the expanded position, one or more of arms 54 are attached to the inner heart surface in order to collect signals from the heart tissue. Each arm comprises a braid 55 of wires and each braid comprises multiple conductive wires to provide the braid mechanical support and flexibility.

In some embodiments, electrodes 58 and sensors 62 are electrically connected to selected pairs of wires in the braid, and these wires are used for transferring signals from the electrodes and sensors. This dual use of the braid allows reduced diameter of each arm 54 and consequently a thinner and more compact distal end 40.

In alternative embodiments, one or more of the electrodes may comprise ablation electrodes or other kinds of electrodes. Additionally or alternatively, various types of sensors can be used, in addition to or instead of position sensors 62.

The expanded position configuration shown in FIG. 2 is sometimes referred to as a basket catheter. The disclosed techniques, however, are not limited to basket catheters and can also be used with other configurations of multi-arm catheters such as PentaRay®.

In the embodiments shown below, the multiple wires in braid 55 are coiled. Generally, however, the wires may be woven into a mesh, coiled into a spiral coil, or configured in any other suitable pattern. In the context of the present patent application and in the claims, the terms "braid" and "braid wires" refer to any suitable configuration of the wires, including various meshed and coiled configurations.

In summary, distal end 40 has multiple arms 54, each arm 54 is surrounded by a braid 55 of wires, and each arm comprises one or more mapping electrodes 58 for electrical potential mapping and one or more position sensors 62 for position and orientation of the distal end. The disclosed technique makes dual use of braid 55 wires in operation— mechanical support and signal transmission. Certain aspects of the use of braid wires for signal transmission are also described in U.S. patent application Ser. No. 14/157,739, filed Jan. 17, 2014, whose disclosure is incorporated herein by reference.

Figure 3:
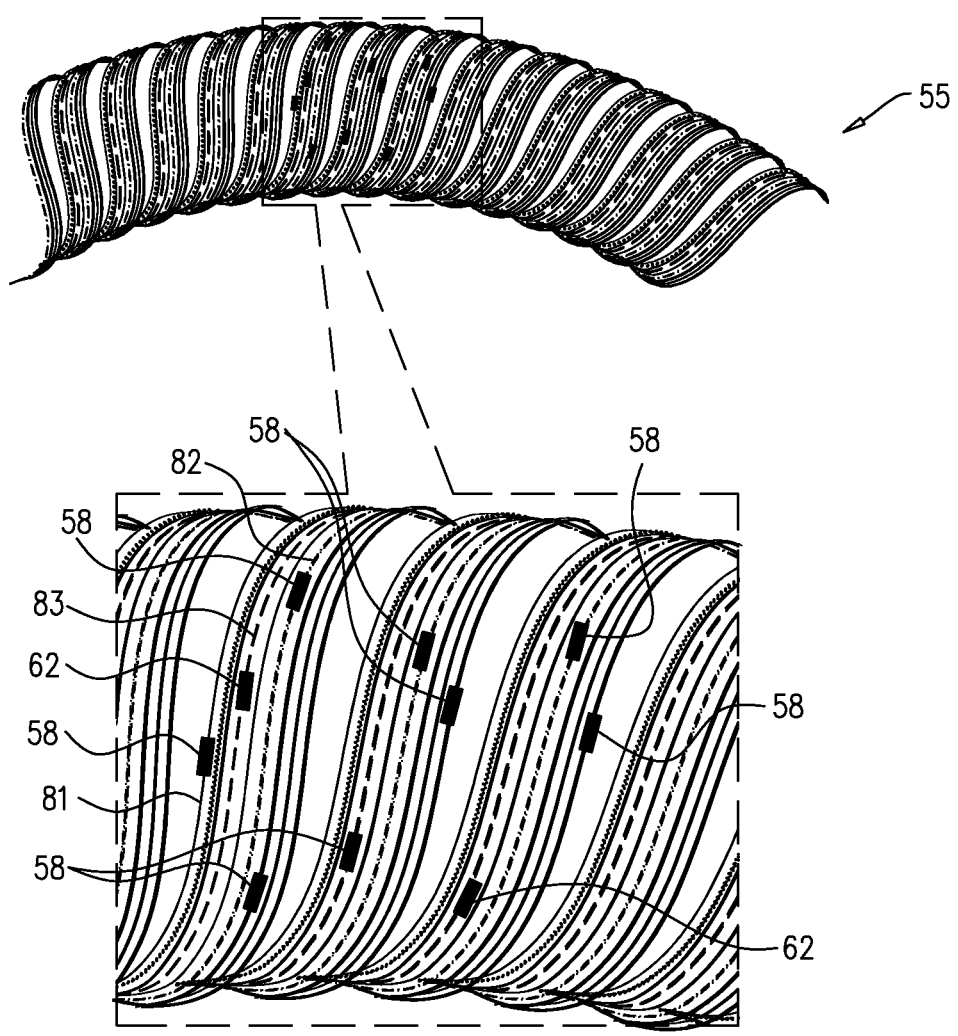
FIG. 3 is a diagram schematically illustrating an arm of a multi-arm catheter with position sensors and mapping electrodes connected via braid wires, in accordance with an embodiment of the present invention.

FIG. 3 is a diagram schematically illustrating wires of a single arm 54 of multi-arm distal end 40, in accordance with an embodiment of the present invention. Braid 55 comprises multiple wires. Each position sensor and each mapping electrode 58 is connected to a respective wire pair selected from the multiple wires of braid 55. The wires used for connecting the sensors and electrodes are electrically isolated, and the isolation is exposed at the appropriate location for connecting the electrode or sensor to the wires.

For example, in FIG. 3, one mapping electrode 58 is connected to a pair of wires 81, position sensor 62 is connected to a pair of wires 83 and an additional mapping electrode 58 is connected to a pair of wires 82. Each of these wires is electrically isolated from the other wires in braid 55.

The wires of braid 55 typically run along the entire length of the catheter. At the proximal end, the wires are connected to console 24. Thus, the electrical signals produced by sensors 62 and electrodes 58 are transferred to console 24 over the selected wires.

In alternative embodiments, additional devices such as one or more ablation electrodes or other kinds of electrodes and sensors can be embedded in one or more arms 54 and connected to console 24 using selected braid wires. In alternative embodiments the distal end may comprise any suitable number of arms 54 and the arms may be arranged in a basket configuration or in any other suitable configuration. Each arm 54 may have any desired number of mapping electrodes, position sensors and/or any desired number of other kind of sensors or electrodes.

FIG. 4 is a flow chart that schematically illustrates a method for electrical potential mapping using catheter 22 of FIG. 3, in accordance with an embodiment of the present invention. The method begins with operator 30 inserting catheter 22, at an insertion step 200.

At an expanding step 210, the operator expands the catheter's multi-arm distal end 40. At an attaching step 220, the operator attaches multi-arm distal end 40 to the inner surface of the desired location of the patient's heart. At an applying step 230, a magnetic field is applied to patient body 28 from magnetic field generators 36. At a measuring step 240, the system measures positions using position sensors 62 and electrical potentials using mapping electrodes 58.

At a signal transfer step 250, processor 42 reads the signals from the position sensors and mapping electrodes via the braid wires of arms 54. In alternative embodiments, braid 55 wires can be used for connecting ablation electrodes or any other suitable device that performs another diagnostic or therapeutic procedure in the patient's body. In a processing step 260, processor processes the signals from the various position sensors and mapping electrodes, so as to generate the electrophysiology map and display the map on image 44 of heart 26 on user display 46.

Although the embodiments described herein mainly address cardiology, the methods and systems described herein can also be used in other applications, such as in Ear, Nose and Throat (ENT) applications.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system, comprising:
   a combination electrophysiological (EP) mapping and position sensing basket catheter, the combination electrophysiological (EP) mapping and position sensing comprising,
   an insertion tube for insertion into a patient body;

multiple arms, which are attached to a distal end of the insertion tube, each arm comprising a braid of wires that traverse the arm, wherein each arm comprises:

embedded electrophysiological (EP) mapping electrodes and embedded magnetic position sensors, wherein the magnetic position sensors are embedded in the same manner as the electrophysiological (EP) mapping electrodes, and a braid of multi-function wires, said multi-function wires adapted to simultaneously provide mechanical support, position sensor signal delivery and electrophysiological (EP) mapping electrode signal delivery, said electrophysiological (EP) mapping electrodes and magnetic position sensors being electrically connected to select wires, wherein the wires connected to the electrophysiological (EP) mapping electrodes and the wires connected to the magnetic position sensors are electrically isolated, said isolation being exposed at the locations for connecting the electrophysiological (EP) mapping electrodes and magnetic position sensors to their respective wires;

wherein the electrophysiological (EP) mapping electrodes are configured to exchange signals over the wires with a system external to the patient body; and wherein the magnetic position sensors are configured to produce position signals that are indicative of respective positions in the patient body, and to transfer the position signals over the wires; and a processor communicating with the combination electrophysiological (EP) mapping and position sensing basket catheter, wherein the electrophysiological (EP) mapping electrodes are configured to produce the signals in response to measured EP potential, and wherein, when the distal end is brought into contact with an inner surface of the patient heart, the electrophysiological (EP) mapping electrodes are adapted to generate potential gradient signals in response to sensed electrical potentials and the magnetic position sensors are adapted to generate position signals in response to sensed external magnetic fields, wherein the processor is adapted to map the electrical potentials as a function of position within the heart cavity, wherein the braid of wires in each arm is coiled into a spiral coil, wherein each of the arms is an entirely braided structure wherein, in each braid, a first electrophysiological (EP) mapping electrode is connected to a first wire, a magnetic position sensor is connected to a second wire, and a second electrophysiological (EP) mapping electrode is connected to a third wire, and wherein the first wire, the second wire, and the third wire are electrically isolated from one another.

2. The system according to claim 1, wherein one or more of the electrodes comprise ablation electrodes that are configured to perform ablation of tissue in response to an ablation signal.

3. A method, comprising:

inserting into a patient body a combination electrophysiological (EP) mapping and position sensing basket catheter, which comprises an insertion tube and multiple arms attached to a distal end of the insertion tube, each arm comprising a braid of wires that traverse the arm, wherein each arm comprises:

embedded electrophysiological (EP) mapping electrodes and embedded magnetic position sensors, wherein the magnetic position sensors are embedded in the same manner as the electrophysiological (EP) mapping electrodes, and a braid of multi-function wires, said multi-function wires adapted to simultaneously provide mechanical support, position sensor signal delivery and electrophysiological (EP) mapping electrode signal delivery, said electrophysiological (EP) mapping electrodes and magnetic position sensors being electrically connected to select wires, wherein the wires connected to the electrophysiological (EP) mapping electrodes and the wires connected to the magnetic position sensors are electrically isolated, said isolation being exposed at the locations for connecting the electrophysiological (EP) mapping electrodes and magnetic position sensors to their respective wires;

expanding the multiple arms into a basket configuration;

providing a processor external to the patient body and communicating with the combination electrophysiological (EP) mapping and position sensing basket catheter;

exchanging signals over the wires between the electrophysiological (EP) mapping electrodes and the processor external to the patient body; and bringing the distal end into contact with an inner surface of the patient heart, wherein exchanging the signals comprises transferring over the wires position signals that are indicative of respective positions in the patient body, wherein the electrophysiological (EP) mapping electrodes are configured to produce the signals in response to measured EP potential, wherein, when the distal end is brought into contact with an inner surface of the patient heart, the electrophysiological (EP) mapping electrodes are adapted to generate potential gradient signals in response to sensed electrical potentials and the magnetic position sensors are adapted to generate position signals in response to the sensed external magnetic fields, wherein the processor is adapted to map the electrical potentials as a function of position within the heart cavity, wherein the braid of wires in each arm is coiled into a spiral coil, wherein each of the arms is an entirely braided structure, and wherein, in each braid, a first electrophysiological (EP) mapping electrode is connected to a first wire, a magnetic position sensor is connected to a second wire, and a second electrophysiological (EP) mapping electrode is connected to a third wire, and wherein the first pair wire, the second wire, and the third wire are electrically isolated from one another.

4. The method according to claim 3, wherein one or more of the electrodes comprise ablation electrodes, and wherein exchanging the signals comprises sending an ablation signal for performing ablation of tissue.

5. A method, comprising:

providing an insertion tube for insertion into a patient body;

attaching to a distal end of the insertion tube multiple arms, each arm comprising a braid of wires that traverse the arm, wherein each arm comprises:

embedded electrophysiological (EP) mapping electrodes and embedded magnetic position sensors, wherein the magnetic position sensors are embedded in the same manner as the electrophysiological (EP) mapping electrodes, and a braid of multi-function wires, said multi-function wires adapted to simultaneously provide mechanical support, position sensor signal delivery and electrophysiological (EP) mapping electrode signal delivery, said electrophysiological (EP) mapping electrodes and magnetic position sensors being electrically connected to select wires, wherein the wires connected to the electrophysiological (EP) mapping electrodes and the wires connected to the magnetic position sensors are electrically isolated, said isolation being exposed at the locations for connecting the electrophysiological (EP) mapping electrodes and magnetic position sensors to their respective wires;

expanding the multiple arms into a basket configuration;

providing a processor external to the patient body and communicating with the insertion tube, exchanging signals over the wires between the electrophysiological (EP) mapping electrodes and the processor external to the patient body; and bringing the distal end into contact with an inner surface of the patient heart coupling to the arms multiple electrodes, and electrically connecting the electrodes to respective selected wires of the braid, so as to exchange signals over the wires with the processor external to the patient body, wherein exchanging the signals comprises transferring over the wires position signals that are indicative of respective positions in the patient body, wherein the electrophysiological (EP) mapping electrodes are configured to produce the signals in response to measured EP potential, wherein, when the distal end is brought into contact with an inner surface of the patient heart, the electrophysiological (EP) mapping electrodes are adapted to generate potential gradient signals in response to sensed electrical potentials and the magnetic position sensors are adapted to generate position signals in response to the sensed external magnetic fields, wherein the processor is adapted to map the electrical potentials as a function of position within the heart cavity, wherein the braid of wires in each arm is coiled into a spiral coil, wherein each of the arms is an entirely braided structure wherein, in each braid, a first electrophysiological (EP) mapping electrode is connected to a first wire, a magnetic position sensor is connected to a second wire, and a second electrophysiological (EP) mapping electrode is connected to a third wire, and wherein the first wire, the second wire, and the third wire are electrically isolated from one another.

* * * * *